United States Patent
Teoh et al.

(10) Patent No.: US 9,308,352 B2
(45) Date of Patent: Apr. 12, 2016

(54) RETENTION MEMBER AND APPLICATION THEREOF

(75) Inventors: Teng Sun Teoh, Penang (MY); Chai Wayne Ng, Penang (MY); Mohd Zairizal Bin Zakaria, Penang (MY); Hang Khiang Chng, Bishan (SG)

(73) Assignee: B. Braun Melsungen AG, Melsungen (DE)

( * ) Notice: Subject to any disclaimer, the term of this patent is extended or adjusted under 35 U.S.C. 154(b) by 85 days.

(21) Appl. No.: 13/168,135

(22) Filed: Jun. 24, 2011

(65) Prior Publication Data

US 2011/0319820 A1      Dec. 29, 2011

(51) Int. Cl.
| | |
|---|---|
| *A61M 5/36* | (2006.01) |
| *A61M 25/06* | (2006.01) |
| *A61M 25/00* | (2006.01) |
| *A61M 5/32* | (2006.01) |

(52) U.S. Cl.
CPC ....... *A61M 25/0606* (2013.01); *A61M 25/0014* (2013.01); *A61M 25/0097* (2013.01); *A61M 5/3275* (2013.01); *A61M 25/0618* (2013.01); *A61M 25/0693* (2013.01); *A61M 2005/325* (2013.01); *Y10T 29/49826* (2015.01)

(58) Field of Classification Search
CPC .......... A61M 25/0693; A61M 25/606; A61M 25/0014; A61M 25/0097
USPC ............. 604/164.01, 164.08, 167.01–167.06, 604/168.01
See application file for complete search history.

(56) References Cited

U.S. PATENT DOCUMENTS

| | | | |
|---|---|---|---|
| 4,365,630 A | 12/1982 | McFarlane | |
| 5,030,205 A | 7/1991 | Holdaway et al. | |
| 5,810,785 A | 9/1998 | Bogert et al. | |
| 6,117,108 A * | 9/2000 | Woehr et al. | 604/110 |
| 2004/0204690 A1 | 10/2004 | Yashiro et al. | |
| 2007/0083157 A1 | 4/2007 | Belley et al. | |
| 2007/0100295 A1 | 5/2007 | Belley et al. | |
| 2008/0091173 A1 | 4/2008 | Belley et al. | |
| 2010/0204660 A1 * | 8/2010 | McKinnon et al. | 604/244 |

FOREIGN PATENT DOCUMENTS

| | | |
|---|---|---|
| WO | WO 99/08742 | 2/1999 |
| WO | WO 99/24092 | 5/1999 |
| WO | WO 2007/103690 | 9/2007 |
| WO | WO 2010/093792 A1 | 8/2010 |

OTHER PUBLICATIONS

Office Action on corresponding foreign application (JP Application No. 2013-515766) from the Japanese Patent Office dated Apr. 21, 2015.

* cited by examiner

*Primary Examiner* — Laura Bouchelle
(74) *Attorney, Agent, or Firm* — Klein, O'Neill & Singh, LLP (57) ABSTRACT

An IV catheter introducer assembly including a catheter hub defining a chamber; a tubular member extending distally from the catheter hub having a length and defining a lumen, the lumen being in fluid communication with the chamber and configured to removably receive an introducer needle. The device also including a retention member disposed within the chamber having a body having a central lumen having a longitudinal length extending along a lengthwise direction to the length of the tubular member and sized to seal against an introducer needle. The retention member including a venting channel having at least a portion formed as a conic helix traversing a surface of the retention member along a radial path to the lengthwise direction.

21 Claims, 6 Drawing Sheets

RETENTION MEMBER AND APPLICATION THEREOF

CROSS-REFERENCE TO RELATED APPLICATION

This is a regular utility application of provisional application Ser. No. 61/358,591, filed Jun. 25, 2010, the contents of which are expressly incorporated herein by reference.

BACKGROUND

1. Field

Embodiments discussed herein generally relate to a medical device used to facilitate the transfer of fluid from a fluid source to a patient, and more specifically, to a retention member used in the medical device, such as an intravenous (IV) catheter introducer assembly, for the prevention of blood backflow and blood leakage.

2. Relevant Art

Health care practitioners administering a catheter will locate the tip of a catheter needle in a vein or artery of the patient. When the needle tip is properly located, a small flow or flash of blood occurs through the hollow needle and into the flash or hub chamber at the proximal end of the needle. The health care practitioner notes the presence of blood in the flash chamber as an indication of proper needle placement, and then advances the catheter into the vascular system and withdraws the needle from the patient, leaving the catheter in place in the blood vessel.

As the needle tip moves to a location proximal of the distal end of the catheter tube, blood also flows under venous or arterial pressure into the catheter. Typically, blood enters the annular space between the outer surface of the needle and the inner wall of the catheter cannula or tube. To a practitioner, this blood flow into the annular space between the needle and the catheter tube confirms successful catheter placement and is typically a quicker feedback than verifying blood in the flash chamber of the needle hub. Usually, this "backflow" of blood is of no consequence because the catheter hub is quickly connected to a tubing set once the needle is withdrawn from the catheter. However, catheters with, for example, needle guards and the like that occupy the catheter hub may become contaminated by the backflow of blood prior to the complete withdrawal of the needle. A contaminated needle guard, for example, subjects health care practitioners to undesirable contact with the patient's blood.

To remedy the possibility of undesirable contact with the patient's blood, many catheters employ plugs, caps or valves, which may be collectively referred to as plug or plugs, to seal the catheter hub from the catheter cannula. However, some of these plugs are not effective to reliably evacuate air, which is needed to allow for the effective flash flow of blood through the space between the catheter tube and the needle. Consequently, it has been a problem to produce a plug that is effective to exhaust air while obviating blood loss following puncture of the vein. In some previously developed air bleeding plugs, only a single narrow opening is provided, which may be so oriented or clogged as to not permit the adequate evacuation of air from the interior of the IV catheter assembly. A clogged or plugged air passage is analogous to requiring blood flow to flow into a dead space.

SUMMARY

The various embodiments of the retention valve have several features, no single one of which is solely responsible for their desirable attributes. Without limiting the scope of the present embodiments as set forth in the claims that follow, their more prominent features now will be discussed briefly.

In one aspect, an IV catheter introducer assembly is provided including a catheter hub defining a chamber; a tubular member extending distally from the catheter hub having a length and defining a lumen, the lumen being in fluid communication with the chamber and configured to removably receive an introducer needle; and a retention member disposed within the chamber having a body having a central lumen having a longitudinal length extending along a lengthwise direction to the length of the tubular member and sized to seal against an introducer needle. The retention member including a venting channel having at least a portion formed as a conic helix traversing a surface of the retention member along a radial path to the lengthwise direction.

In another aspect, an IV catheter introducer assembly is provided including a catheter hub defining a chamber; a tubular member extending distally from the catheter hub and defining a lumen, where the lumen is in fluid communication with the chamber and extends along a lengthwise axis; a needle hub having a needle extending through the lumen of the tubular member; and a retention member defining a central lumen disposed coaxially with the lengthwise axis of the retention member. The retention member including a distal end, a proximal end, and a fixation portion configured to sealingly engage with a portion of the catheter hub. The retention member further including a continuous venting path defined on an exterior surface starting adjacent the distal end and extending helically outward towards the proximal end.

In still yet another aspect, an IV catheter introducer assembly is provided including a catheter hub, which defines a chamber, having a tubular member, which defines a lumen, extending distally from the catheter hub, where the lumen is in fluid communication with the chamber; and a needle hub having a needle extending through the lumen of the tubular member. The assembly also includes a retention member having a distal surface, a proximal surface, and an outer radial surface. The retention member defines a central lumen disposed coaxially with a lengthwise axis of the retention member. The retention member includes a first portion of a continuous venting path defined on the distal surface of the retention member and extending helically outward toward an outer diameter of the retention member, a second portion of the continuous venting path defined on the proximal surface of the retention member extending helically outward toward the outer diameter of the retention member, and a radial venting path defined on the outer radial surface of the retention member coupling the first portion to the second portion.

Another feature of the present device and assembly is an intravenous (IV) catheter introducer assembly comprising a catheter hub comprising a retention member having a bore and a longitudinal length of X and a venting path length of at least 2X, and wherein X is number representing a length. Wherein the venting path length comprises a spiral path length. Wherein the venting path length comprises a radial path length and an axial channel both formed upon an exterior surface of the retention member. Wherein the venting path length can comprise at least 3X and comprises a non-linear vent path formed along an exterior surface of the retention member.

In one embodiment, the retention member comprises a plurality of base walls of increasing diameters formed on an exterior surface thereof from a distal end towards a proximal direction.

In one embodiment, the retention member comprises a plurality of base walls of decreasing diameters from a proximal end towards a distal direction.

In another aspect of the present disclosure, a method for assembling a catheter assembly is provided. The method comprising mounting a needle with a needle tip to a needle hub; mounting a catheter tube with a lumen to a catheter hub, the catheter hub comprising an interior surface defining an interior cavity. The method further comprising placing a retention member in the interior cavity of the catheter hub, the retention member comprising a bore, a distally facing surface, and a proximally facing surface and placing the needle through the bore of the retention member and the lumen of the catheter tube. In a specific example, the retention member comprises a longitudinal length of X and a venting path length of at least 3X, and wherein X is number representing a length.

This brief summary has been provided so that the nature of the invention be understood quickly. A more complete understanding of the invention may be obtained by reference to the following detailed description of the embodiments thereof concerning the attached drawings.

BRIEF DESCRIPTION OF THE DRAWINGS

The various embodiments of the present IV catheter introducer assembly are now discussed in detail with an emphasis on highlighting the advantageous features. These embodiments depict the novel and non-obvious features of the IV catheter introducer assembly shown in the accompanying drawings, which are for illustrative purposes only. These drawings include the following figures, in which like numerals indicate like parts.

DETAILED DESCRIPTION

The following detailed description describes the present embodiments with reference to the drawings. In the drawings, reference numbers label elements of the present embodiments. These reference numbers are reproduced below in connection with the discussions of the corresponding drawing features.

Figure 1A:
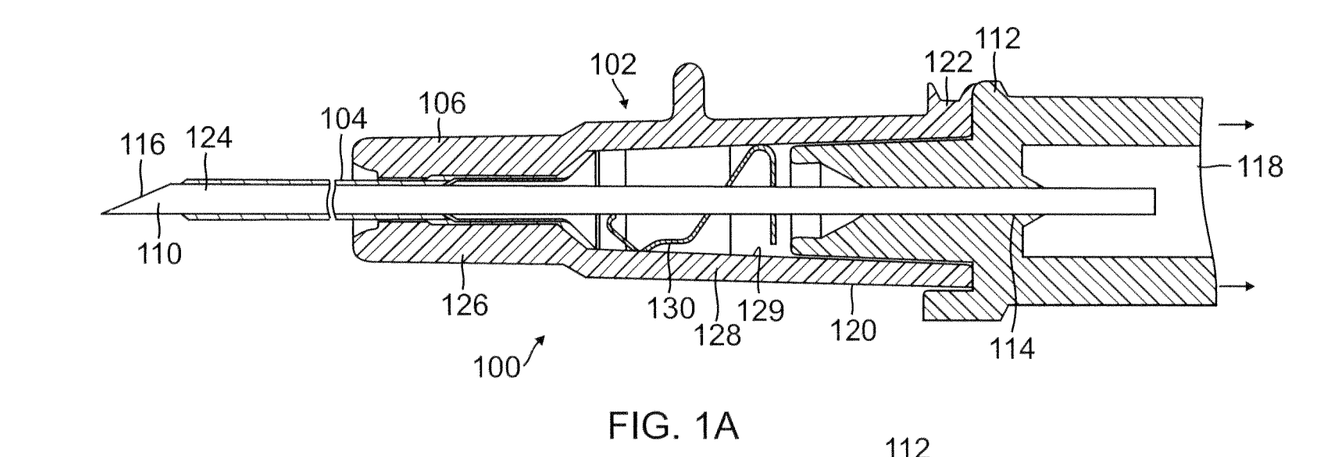
FIG. 1 is a side view of an IV catheter introducer assembly in accordance with an embodiment.
Figure 1B:
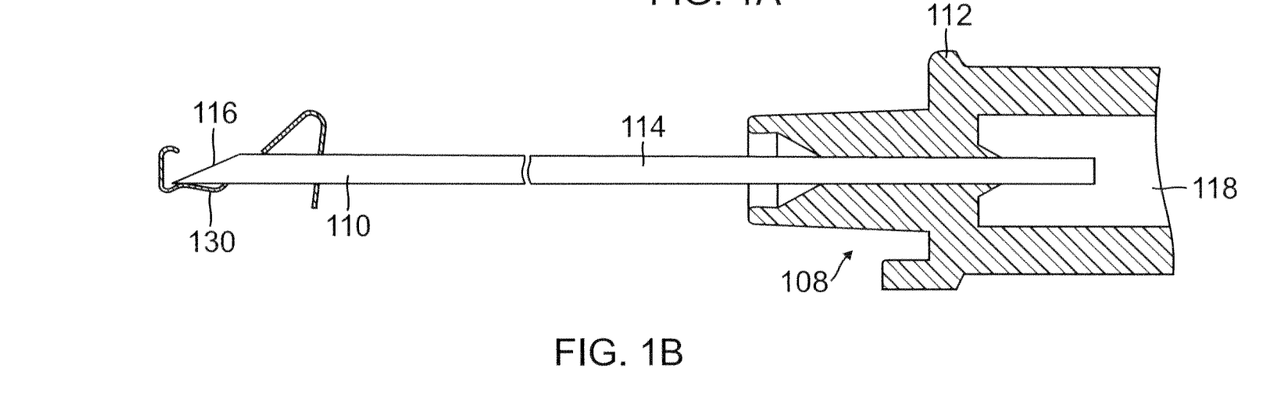

FIGS. 1A and 1B are side views of an IV catheter introducer assembly 100 (hereinafter "catheter assembly 100") in accordance with the practice of the present disclosure. The catheter assembly 100 includes a catheter 102, which includes a flexible tubular catheter or catheter tube 104 mounted to a catheter hub 106 in a conventional manner. The catheter assembly 100 also includes a needle assembly 108, which includes an introducer needle 110 mounted to a needle hub 112 also in a conventional manner.

In one embodiment, the needle 110 further includes a needle shaft 114 having a needle tip 116 disposed at the distal end of the introducer needle 110. The proximal end of the introducer needle 110 extends into a flash chamber 118 at a proximal end of the needle hub 112. In an exemplary embodiment, the needle hub 112 may be made of a transparent material, such as, for example, a transparent or translucent plastic, so that when the introducer needle 110 is successfully inserted into a patient's vein or artery, the backflow of blood may be observed running through the introducer needle and into the flash chamber 118.

In one embodiment, the catheter hub 106 includes an integrally molded body 120 having a distal hub section 126 that defines an axial cylindrical inner catheter passageway having dimensions designed to accept and fixedly attach the tubular catheter 104 therein, and a larger diameter proximal hub section 128 that defines a hub chamber 129. Conventional Luer fitting 122 may be formed on the proximal end of the catheter hub 106 to provide a connection point for IV supply lines and the like with similar taper once the catheter insertion process is complete.

In one embodiment, it should be noted that the needle assembly 108 may further include a safety spring clip or a needle guard 130 that is slideably mounted to the introducer needle 110 and actuated to protect health care practitioners from inadvertent needle sticks. An exemplary catheter assembly including a needle guard is described in U.S. Pat. No. 6,117,108, which is hereby expressly incorporated by reference in its entirety for all purposes. However, other needle guards may be used without deviating from the spirit and scope of the present invention, such as those disclosed in U.S. Pat. Nos. 7,608,057; 7,264,613; 6,709,419; and 7,637,887; and Ser. No. 10/954,041 filed Sep. 28, 2004; Ser. No. 10/677,810 filed Oct. 1, 2003; Ser. No. 10/520,325 filed Sep. 12, 2005; and Ser. No. 11/496,769 filed Jul. 31, 2006, the contents of each of which are expressly incorporated herein by reference in their entirety for all purposes. As presently contemplated, the needle guard may have the following one or more characteristics: (1) an opening formed on a proximal wall to engage an enlarged section on the needle shaft, such as a bulge, a crimp, or a sleeve fixed to the needle, (2) a canting surface that cants to grip the surface of the needle when activated, (3) made from multiple parts or components and assembled together to form an integrated guard, (4) made from a singularly formed component or material, (5) be disposed in a separate guard housing located between the needle hub 112 and the catheter hub 106, (6) include side walls so that the needle guard not only covers the needle tip when in the guarded position but also the radial surfaces of the needle near the needle tip, (7) include one arm, two arms, or more than two arms for moving to a blocking position to block the needle tip, (8) include a tether to limit distal advancement of the needle guard beyond the needle tip, and/or (9) be configured to grab the catheter hub, either the inside surface of the catheter hub or outside surface of the catheter hub, in a ready position and during retraction of the needle relative to the catheter hub.

In the ready position shown in FIG. 1A, at least a substantial portion of the needle shaft 114 is disposed and extends within a lumen defined through the tubular catheter 104, with the needle tip 116 projecting past the distal tip or opening 124 of the tubular catheter 104. The needle guard 130 is disposed within the hub chamber 129.

The catheter assembly 100 operates by inserting the tubular catheter 104 and needle 110 into a vein or artery of a patient and then withdrawing the needle 110 while leaving the tubular catheter 104 connected to the patient. In an exemplary embodiment, the withdrawal of the inserted needle is performed by firmly gripping the catheter hub 106 and preventing the catheter hub 106 from moving, such as by pressing the catheter hub against the skin, while at the same time gripping the needle hub 112 and then withdrawing the needle 110 by pulling or sliding the needle hub 112 proximally relative to the catheter hub to separate the needle 112 from the tubular catheter 104.

In one embodiment, as the needle 110 is being withdrawn from the patient, the protective needle guard 130 located within the hub chamber automatically snaps into a deployed or protective position in which the needle guard blocks the distal needle tip 116 to prevent accidental contact by the health care practitioner with the needle tip (FIG. 1B).

Figure 2A:
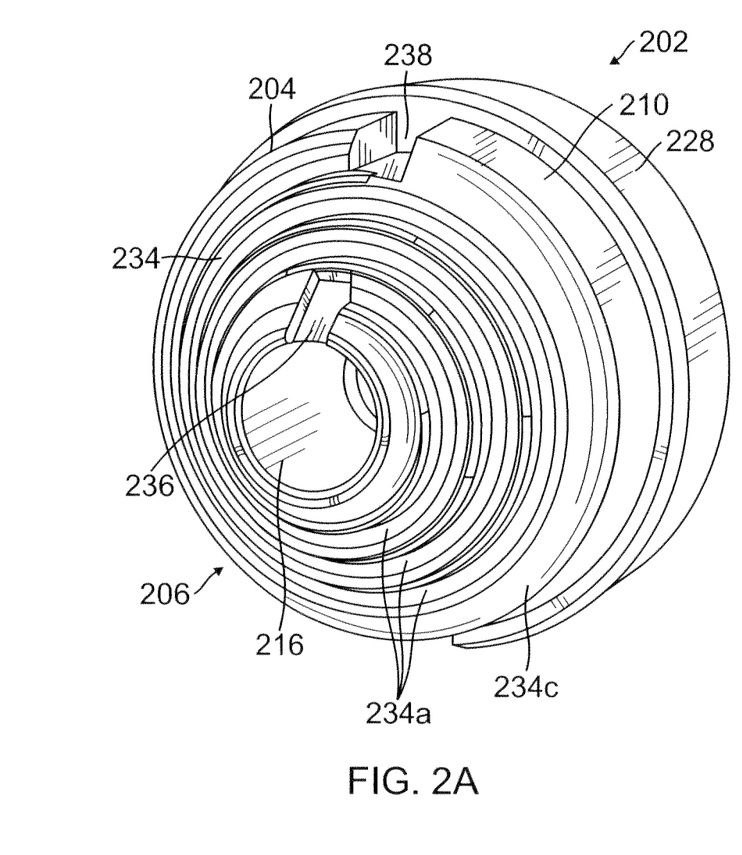
FIGS. 2A, 2B, 2C and 2D are front, rear and bottom perspective views, a side view, and a bottom perspective view, respectively, of a retention member in accordance with an embodiment.
Figure 2B:
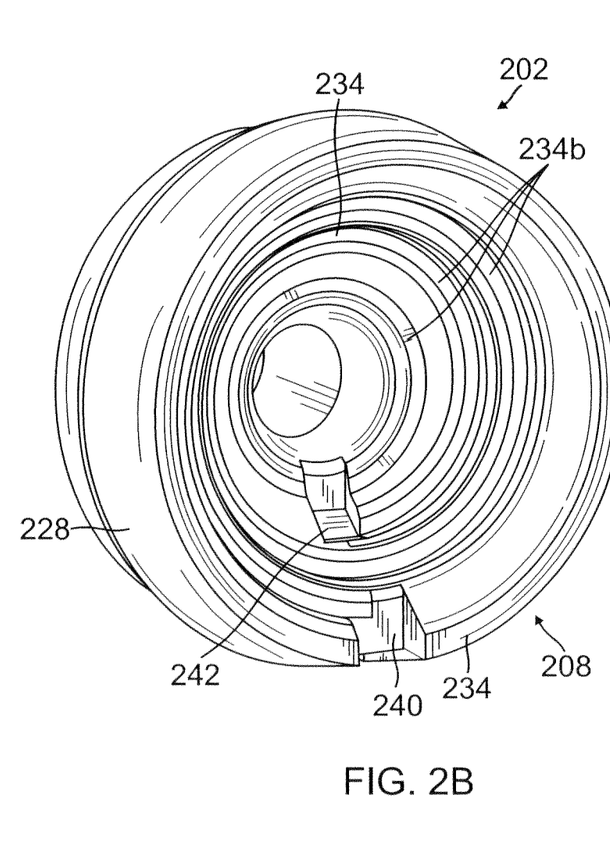
Figure 2C:
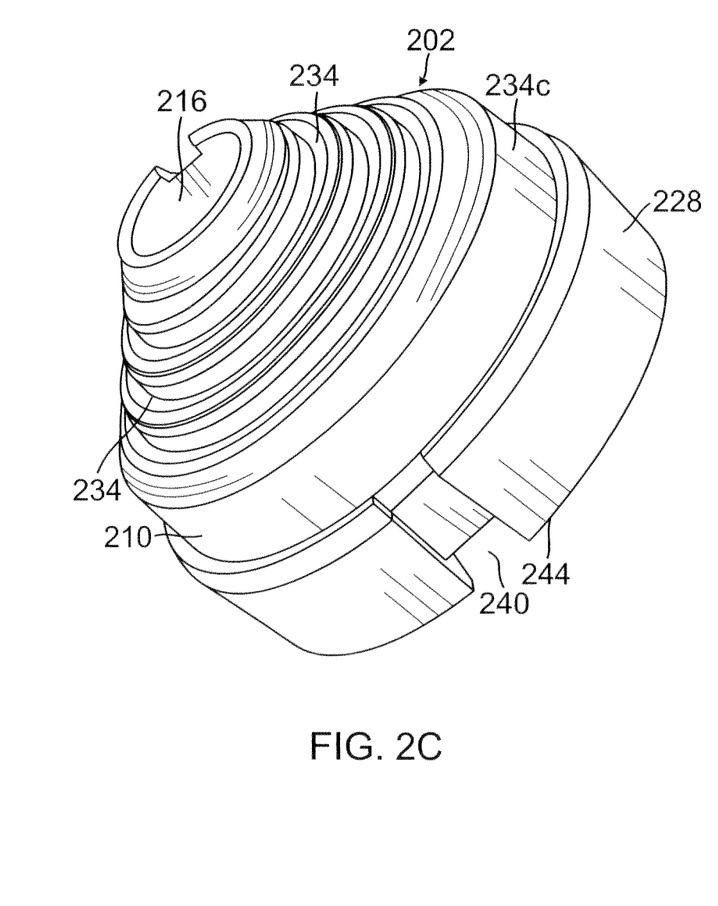
Figure 2D:
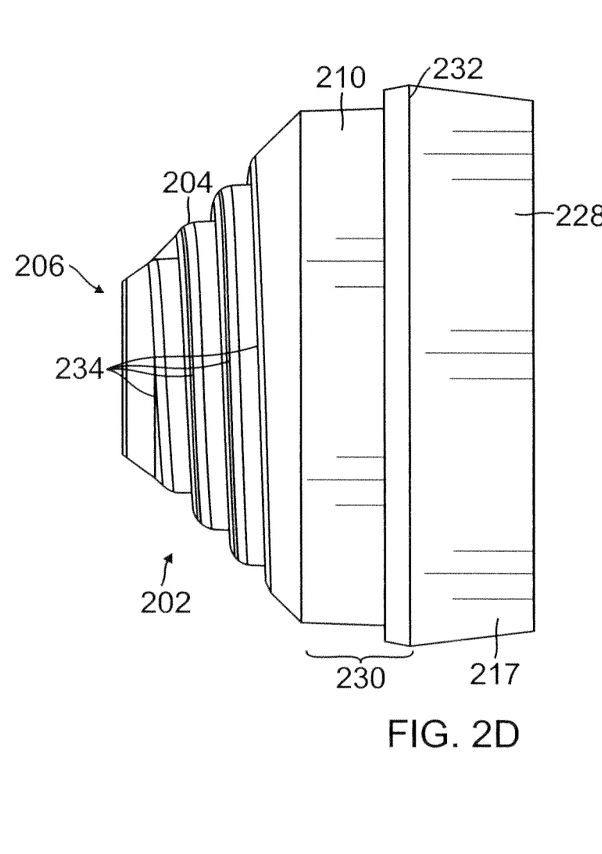

FIGS. 2A, 2B and 2C are front, rear and side perspective views, respectively, and FIG. 2D is a side view of a retention member 202 in accordance with an embodiment. The retention member 202 provides an air venting system for use in a catheter introducer assembly, such as the catheter assembly 100 shown in FIG. 1 and more specifically the catheter hub of FIG. 4. As further discussed below, the retention member 202 can also delay blood flashback into the flash chamber to permit more time for a practitioner to manipulate the catheter assembly.

In one embodiment, the retention member 202 includes a body 204 having a tapered section between a small diameter apex 214, such as an end with a distal most end point having a small diameter, and an enlarged base portion 217 (FIG. 2D). The body 204 having a distal or distally facing surface 206, a proximal or proximally facing surface 208 (FIG. 2B) and an outer radial surface 210. In one embodiment, the end 214 of the body 204 projects distally when positioned in the catheter hub 106 (FIG. 1A) for ease of insertion into the catheter hub and to properly mate in the conically shaped transition section (see FIG. 4) between the distal hub section 126 and the proximal hub section 128 of the catheter hub 106. The retention member 202 may be fabricated by any conventional methods, such as by molding or casting using an elastomer, a thermoplastic elastomer, or low density thermoplastic. Because the retention is made from an elastic material, it may be wedged inside the catheter hub 106 and remain there by the wedging action. Alternatively, a mechanical latch arrangement, such as a detent or snap-fit mechanism, may be used to secure the retention member to the catheter hub. Still alternatively or in addition thereto, glue or adhesive may be used to secure the retention member to the catheter hub.

Figure 3:
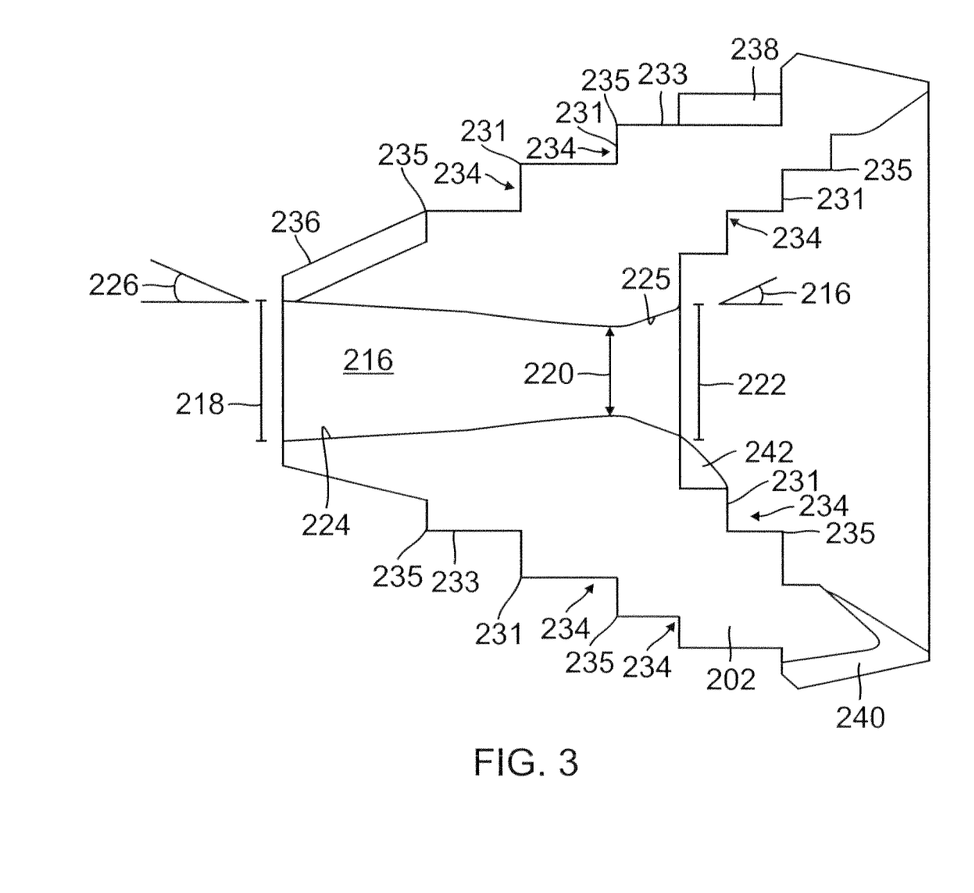
FIG. 3 is a cross-sectional view of the retention member in accordance with an embodiment.

FIG. 3 is a cross sectional view of the retention member of FIG. 2D in accordance with an embodiment. As shown, for example in FIGS. 2A-2D and FIG. 3, the retention member 202 defines a central lumen 216 disposed coaxially with a lengthwise axis of the retention member 202. In one embodiment, the central lumen 216 comprises a distal inside diameter 218, an internal inside diameter 220, and a proximal inside diameter 222. The internal inside diameter 220 of the central lumen 216 is sized and shaped to seal against the introducer needle 110 when the introducer needle 110 is disposed within the central lumen 216. In one embodiment, the central lumen 216 has a first tapered surface 224 located between the distal inside diameter 218 and the internal inside diameter 220 and a second tapered surface 225 located between the internal inside diameter 220 and the proximal inside diameter 222. In an embodiment, the first and second tapered surfaces 224, 225 are tapered relative to the longitudinal axis of the central lumen 216 at an angle 226 of between about 3 and 15 degrees, preferably about 5-10 degrees. In one embodiment, the taper surface has a constant or uniform angle. In another embodiment, the tapered surface has a complex or non-uniform angle. As used herein, terms such as first, second, proximal and distal are relative terms and are not intended to be limiting.

As best shown in FIG. 3, in some embodiments, the distal inside diameter 218 and the proximal inside diameter 222 are formed greater than the interior inside diameter 220, which creates a central lumen having an internal reduced cross-section. The reduced internal diameter 222 seals the needle shaft along a single point or small area contact rather than a line contact to reduce friction during insertion and removal of the needle. In these embodiments, the relatively larger distal inside diameter 218 minimizes the pressure loss due to expansion of the central lumen 216, while the relatively larger proximal inside diameter 222 minimizes pressure loss due to the contraction of the central lumen 216. The distal inside diameter 218 may be equal to, larger than, or slightly smaller than the proximal inside diameter 222. More preferably, the distal inside diameter 218 is larger than the proximal inside diameter 222.

Referring again to FIGS. 2A-2D, in one embodiment, the retention member 202 includes a fixation portion 228 positioned adjacent and proximal to the outer radial surface 210 at the proximal end of the retention member 202. As shown in FIG. 2D, a transition area 230 between the outer radial surface 210 and the fixation portion 228 forms a raised rib member 232 disposed radially around the body 204. The raised rib member 232 includes a raised surface configured to be compressed when the retention member 202 is disposed within the hub chamber 106 and forced with a compression-fit against an interior surface of the hub chamber 106. When compressed against the interior surface, the raised rib member 232 forms a fluid seal or pressure boundary against the interior surface of the catheter hub.

Referring again to FIGS. 2A-2D and FIG. 3, a continuous venting path or venting channel 234 is defined on the distal, proximal and radial surfaces of the retention member 202. As understood from FIG. 3, in one embodiment, portions of the venting path 234 are defined by side walls 231 extending perpendicular from a base wall 233 terminating at upper edges 235 on an upper end of the side walls. The venting path 234 allows air to pass between the distal side of the retention member to the proximal sides of the retention member 202 and vent out to the atmosphere. However, in accordance with aspects of the present method, device, and assembly, the retention member permits venting in a substantially prolonged and spiral path to delay the flow of blood that has ingressed into the venting path 234 and into the interior cavity of the catheter hub 106. The delay allows more time for a practitioner to connect to or otherwise manipulate the catheter hub.

In one embodiment, as shown in FIG. 2A, the distal surface 206 of the retention member 202 defines a first portion 234a of the continuous venting path 234, a first vent channel 236, which may embody a cut-out, and a second vent channel 238, which may cutout. As described in detail below, the first and second vent channels 236, 238 are operationally coupled (i.e. configured to allow air or fluid to traverse therebetween) to the first portion 234a of the venting path 234. This configuration provides a means for air to vent from the tubular catheter 104 while the retention member 202 otherwise remains in sealing engagement with the catheter hub 106 and the introducer needle 110.

In one embodiment, the first vent channel 236 is formed proximate the distal inside diameter 218 of the central lumen 216 (FIG. 3) and extends longitudinally to the first portion 234a (FIG. 3) of the continuous venting path 234. More particularly, the first vent channel 236 terminates at the first upper edge 235 of the first portion 234a. As the body 204 of the retention member 202 increases in diameter in the proximal direction, the first portion 234a of the venting path 234 traverses proximally along the lengthwise longitudinal direction in a spiraling helical path. Thus, the first portion 234a forms the conical helix about the longitudinal axis of the retention member 202 as the first portion 234a extends toward the raised rib 232. A second end of the first portion 234a is operationally coupled to the second vent channel 238. In one embodiment, the second vent channel 238 is defined and positioned to extend longitudinally across the outer radial surface 210 of the retention member 202. In another embodiment, the second vent channel 238 is slanted or tapered as it extends across the outer radial surface 210 of the retention member 202. The first vent channel 236 may similarly be slanted or tapered near the distal end.

As shown in FIG. 2B, in one embodiment, the proximal facing surface 208 of the retention member 202 defines a second portion 234b of the continuous venting path 234, a third vent channel 240, and a fourth vent channel 242, which can be viewed as cut-outs formed generally in an axial direction as compared to the spiral vent paths of the second portion 234b. However, the third and fourth vent channels 240, 242, may have a slant or taper and not formed as true axial vent paths. As described in detail below, the third and fourth vent paths 240, 242 are operationally coupled to the second portion 234b of the continuous venting path 234. In one embodiment, as shown in FIG. 2D, the third vent channel 240 extends longitudinally from the outer radial surface 210, across the fixation portion 228, and around a circumferential edge 244 of the proximal surface 208 (FIG. 2C). As shown in FIGS. 2B and 2C, the third vent channel 240 extends into the proximal surface 208 until it is operationally coupled to a first end of the second portion 234b of the continuous venting path 234.

In one embodiment, the second portion 234b extends from the third vet 240 in a spiraling helical path towards the longitudinal axis of the body 204 of the retention member 202. The second portion 234b of the continuous vent path 234 traverses distally from the third vent cutout 240 along the radial lengthwise longitudinal direction of the body 204 in a distal direction towards the fourth vent channel 242. The second venting portion 234b of the continuous venting path 234 forms a conical helix about the longitudinal axis of the retention member 202 as the second portion 234b radiates in towards an inner diameter of the retention member 202. A second end of the second portion 234b is operationally coupled to the fourth vent channel 242 (FIG. 2B). The fourth vent channel 240 is defined and positioned to extend longitudinally from the second end of the second portion 234b to the proximal inside diameter 222 (FIG. 3) of the retention member 202.

In one embodiment, as shown in FIG. 2C, the outer radial surface 210 defines a radial venting path or third portion 234c of the venting path 234. The radial venting path 234c extends radially around at least a portion of the circumference of the retention member 202 and is operationally coupled to the second vent cutout 238. By extending radially around the outer radial surface 210, the third vent path portion 234c effectively directs gas and blood flow from one radial point at the second vent channel 238 to a different radial point along the outer radial surface 210 to the third vent channel 240. As an example, if the second vent channel 238 is located at the 12 o'clock position and the third vent channel 240 is located at the 6 o'clock position, the third portion 234c is configured to direct air and blood flow from the 12 o'clock position to the 6 o'clock position along the outer radial surface 210. At the third vent channel 240, i.e., at the 6 o'clock position, the vent path operationally couples to the radial venting path of the second portion 234b of the continuous vent path 234, on the proximally facing surface 208 of the retention member 202.

In this manner, the first portion 234a, the second portion 234b), and the radial venting path 234c of the continuous venting path 234 are operationally coupled to one another to allow air (or fluid) to flow between the distal side of the retention member 202 and the proximal side of the retention member 202. Said differently, the first portion, the second portion, and the third portion are in fluid communication with one another. The retention member 202 is also understood to include plurality of fluid flow and venting paths comprising a distal to proximal vent path along a first portion of the vent flow and a proximal to distal path along another portion of the vent flow before entering the flash chamber. Still further, the retention member 202 is understood to include a path comprising a spiral fluid pathway of increasing radial surface area in the distal to proximal direction. In one specific example, the same retention member 202 further includes a spiral pathway of decreasing radial surface area in the proximal to distal direction. In a specific example, the distal to proximal direction comprises a fluid path formed along the distally facing surface 206 and the proximal to distal direction comprises a fluid path formed along the proximally facing surface 208.

In one embodiment, the helical path length of the continuous venting path 234 provides an equivalent linear path length that is greater than the longitudinal length of the retention member 202. Thus, the volume of air that is allowed to traverse between the distal side and the proximal side of the retention member 202 may be greater than the volume of other retention members not having a same longitudinal length. Said differently, for the same gas flow, the current retention member causes the flow to take longer to flow from the space between the catheter tube and the needle and into the flash chamber than for a comparable device without the same retention member. In one embodiment, a total combined venting path length of the first portion 234a, the second portion 234b, and the radial venting path 234c is about 5% or more, preferably about 20% or more, and more preferably about 100% or more, such as 700%, of the physical longitudinal length of the retention member 202 measured from its proximal edge to its distal edge. In one embodiment, the venting path length has a length of between about 25 mm and 45 mm. The straight length of the longitudinal length of the retention member measured from a proximal end edge to a distal end edge is about 3.0 mm to about 4.5 mm. Thus, a further feature of the present embodiment is a retention member having a longitudinal length of X measured from its proximal edge to its distal edge and a venting path length of at least 2X, such as 3X to 7X. In a specific embodiment, the vent path length is about 10X, where X is understood to be a length of the retention member using either the Metric or English measurement system, for example 3 mm or about 0.118 inch.

Figures 5A, 5B:
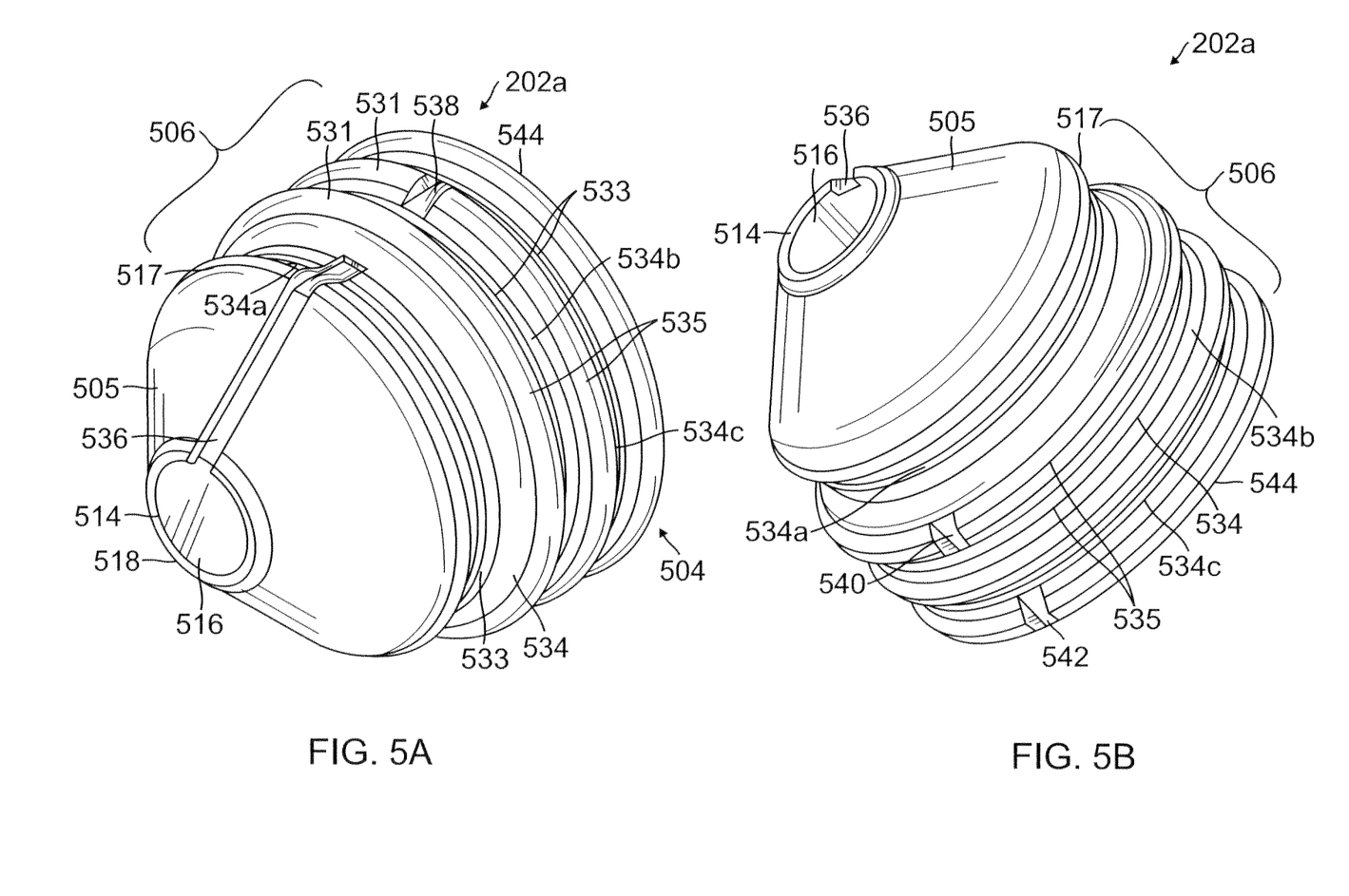
FIGS. 5A and 5B are front and bottom perspective views, respectively, of a retention member in accordance with an alternative embodiment.

FIGS. 5A and 5B are front and bottom perspective views, respectively, of a retention member 202a in accordance with an alternative embodiment. In this alternative embodiment, the retention member 202a includes many of the features of and performs functionally similarly to the retention member 202 of FIGS. 2C and 2D except for those differences described below. In one embodiment, the retention member 202a includes a body 504 having a distally facing section 505 that is generally tapered between a small diameter end having an apex 514 and an enlarged base portion 517. The body 504 also has a radial surface section 506 extending generally between the enlarged base portion 517 and a rear or proximal edge 544 of the radial surface section 506. The internal or proximally facing surface (not shown) of the body 504 includes a smooth tapered wall. As such, the vent path is confined to the exterior surface of the alternative retention member and the interior surface of the catheter hub. In another embodiment, the proximally facing surface (not shown) has an inwardly radial surface section for increasing the flow path, similar to the distally facing surface.

Referring again to FIGS. 5A and 5B, a continuous venting path or venting channel 534 is defined on the radial surface section 506 of the retention member 202a. As understood from FIGS. 5A and 5B, the channels that form the venting path 534 are defined by a series of channel walls 531 that extend perpendicular from a base wall 533 terminating at upper edges 535 on an upper end of the channel walls. The channel walls 531 are disposed along the radial surface section 506 and provide a boundary or barrier between the channels. The channel walls 531 are substantially concentric around a central lumen 516 defined through the retention member 202a along a central axis thereof. The venting path 534 allows air to pass over the radial surface section 506 of the retention member 202a in a substantially prolonged and circular path to delay the flow of blood that has ingressed into the venting path 534.

In this embodiment, as shown in FIGS. 5A and 5B, the channel walls 531 of the retention member 202a define a first vent section 534a, a second vent section 534b, and a third vent section 534c of the continuous venting path 534. It should be understood that more or fewer vent sections may be incorporated into the retention member 202a. A first vent channel in the shape of a cutout 536 is positioned on and extends across the distally facing section 505. In this embodiment, the first vent channel 536 is defined proximate the distal surface inside diameter 518 of the central lumen 516 and extends proximally and longitudinally through the enlarged base portion 517. Thus, the first vent channel 536 operationally places the area adjacent the apex 514 in fluid communication with the first vent section 534a of the continuous venting path 534. As compared to the first vent channel 236 of the first retention member 202, the present first vent channel 536 is about two times to three times longer since it extends the entire distal cone section 505 of the retention member 202a.

A second vent cutout 538 is positioned on a first side of the radial surface section 506 substantially in longitudinal alignment with the first vent cutout 536. The second vent cutout 538 is defined and positioned to extend across the channel wall 531 dividing the second vent section 534b and the third vent section 534c. A third vent channel or cutout 540 and a fourth vent channel or cutout 542 are positioned on an opposite side or a second side of the distal surface 506. As shown in FIG. 5B, on the opposite side, the third vent cutout 540 is defined and positioned to extend across the channel wall 531 dividing the first vent section 534a and the second vent section 534b. The fourth vent cutout 542 is defined and positioned to extend across the circumferential proximal edge 544 of the radial surface section 506.

The vent sections 534a, 534b, and 534c circumvent the retention member 202a around the central lumen 516. The vent sections are divided by the channel walls 531. Each of the vent sections operationally couples to an adjacently positioned channel via the second and third vent cutouts 538 and 540 to effectively couple the vent sections together to form the circularly oriented venting path 534. That is the first vent section 534a, the second vent section 534b, and the third vent section 534c are each in fluid communication with one another via the vent cutouts.

Operationally, the retention member 202a allows fluid to flow circumferentially in the vent sections 534a, 534b, 534c of the retention member while advancing the fluid and gas from the distal apex 514 to the proximal edge 544 of the retention member 202a via the vent cutouts 536, 538, 540, 542. For instance, fluid and gas may flow from an area adjacent the apex 514 and into the first vent cutout 536, which crosses over the enlarged base portion 517 into the first vent section 534a. The fluid and gas may then flow circumferentially in the first vent section 534a in either radial direction relative to the first vent cutout 536. When the fluid reaches the third vent cutout 540 positioned on the opposite side of the body 504, the fluid may then flow across the third vent cutout 540 and into the second vent section 534b. The fluid may then flow circumferentially in the second vent section 534b, in either radial direction relative to the third vent cutout. When the fluid reaches the second vent cutout 538 positioned on the opposite side of the body 504, the fluid then flows across the second vent cutout 538 and into the third vent section 534c. The fluid may then flow circumferentially in the third vent section 534c, in either direction relative to the second vent cutout 538. When the fluid reaches the fourth vent cutout 542 positioned on the opposite side of the body 504, the fluid then flows across the fourth vent cutout 542 and over the circumferential edge 544 into the catheter hub.

By providing a non-direct fluid path, i.e., by providing channels and cut-outs, so that fluid travels a greater distance than the surface length of the retention member measured from the proximal end to the distal end, blood flash back is delayed before reaching the flash chamber of the needle hub. This in turn allows a practitioner more time to treat his or her patient with less leakage concern. In one example, the surface length of the retention member 202a is X and the non-direct fluid path is at least 2X, such as 3X to 10X. The alternative vent path may be placed inside the catheter assembly and held therein by compression fit between the slightly larger outside diameter of the base portion and the interior surface of the catheter hub.

Figure 4:
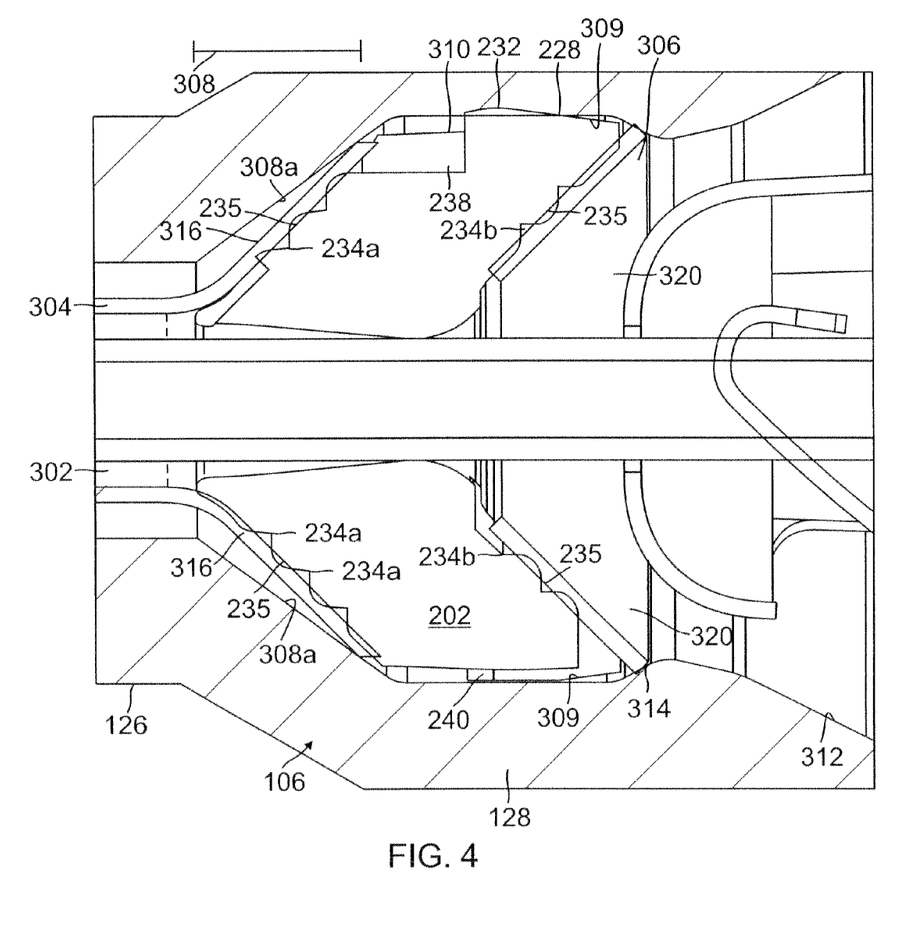
FIG. 4 is a cross-sectional view of the catheter hub including a retention member in accordance with an embodiment.

Referring now to FIG. 4, a cross-sectional view of a catheter hub 106 is shown. The hub is shown with the retention member 202 in accordance with aspects of the present device, assembly and method. In this embodiment, the catheter hub 106 includes a distal hub portion 126 that defines an axial passageway 302 formed therethrough. The catheter hub 106 also includes the proximal hub section 128 having an inner wall surface 309 defining a catheter chamber 306 and a conically shaped transition section 308 that has a tapered surface extending between the distal hub portion 126 and the proximal hub portion 128. The inner wall surface 309 includes a tapered section 308a of the transition section 308, a retention section 310, adjacent and proximal to the tapered section 308a and an inner wall section 312, adjacent and proximal to the retention section 310.

In one embodiment, a retention bump 314 is provided on the inner wall surface 309 between the retention section 310 and the inner wall section 312. The retention bump 314 is formed as a circumferentially disposed raised rib member projecting away from the inner wall surface of the catheter hub towards the central axis of the catheter chamber 306. The retention bump 314 is used to help restrain the retention member 202 inside the catheter hub, via a conical retention washer 320 engaging the retention section 310, as further described below.

Referring again to FIG. 4, a sleeve 304 may have a distal portion received within the passageway 302 to engage with the tubular catheter 104 and hold the tubular catheter in position. A proximal portion of the sleeve 304 is disposed outside the passageway 302 extending into the catheter chamber 306. The proximal portion of the sleeve 304 opens or flares out into a conical shaped portion 316 that has substantially the same taper as the tapered inner wall 308a forming the transition section 308. Thus, when the distal portion of the sleeve is received in the passageway 302, the distal face of the conical shaped portion 316 may abut and lay substantially against the tapered inner wall 308a.

In one embodiment, the retention member 202 is positioned into the catheter chamber 306 so that the distal facing surface 206 of the body 204 of the retention member 202 substantially abuts the proximal face of the conical shaped portion 316 of the sleeve 304 positioned against the tapered inner wall 308a of the transition section 308. In this embodiment, the upper edges 235 of the venting path 234 contact the proximal face of the conical shaped portion 316. It should be understood that in some embodiments in which the sleeve 304 may not be used, the upper edges 235 of the venting path 234 may contact the tapered inner wall 308a directly.

The fixation portion 228 at the proximal end of the body 204 contacts the wall of the retention section 310 of the catheter hub. The raised rib member 232 of the fixation portion 228 positioned adjacent and proximal to the outer radial surface 210 at the proximal end of the retention member 202 is compressed against the wall of the retention section 310 of the inner wall surface 309 of the catheter chamber 306.

To secure the retention member 202 into position, a retention washer 320 is placed into the retention section 310 and against the proximal facing surface 208 of the retention member 202. The washer 320 may be a substantially bell, cone, or frustoconical shaped washer so as to conform to the shape of the proximal facing surface of the retention member 202. The washer 320 is secured into the retention section 310 to contact and contain the retention member 202 between the tapered inner wall 308a and the washer 320. The cone shaped washer 320 may be fastened in the retention section by abutting the same against the retention bump 314 or through use of an adhesive or similar means or both. In one embodiment, the washer 320 may be made of a flexible or resilient material. In another embodiment, the washer is made from a hard thermoplastic or engineered plastic material. In yet another embodiment, the washer is made from a metal material, such as from stainless steel.

In one embodiment, the large diameter end of the cone shaped washer 320 has a diameter that fits within the diameter of the retention section 310 but is larger than the diameter of the inwardly projecting retention bump 314 formed at the proximal end of the retention section 310. Thus, as the cone shaped washer 320 is forced distally into the retention section 310 to secure the retention member 202, the edge of the large diameter end of the washer 320, or the retention bump 314 or both, flexes so that it can be squeezed and moved over the retention bump 314. However, once over the retention bump 314, the large diameter end of the washer expands back to its primary diameter causing the washer 320 to be physically restrained by the retention bump 314 from proximal movement, thus also securing the retention member 202 from proximal movement as well. The washer 320 is configured to trap fluid and gas between its distally facing wall surface and the vent paths of the proximally facing wall surface 208 of the retention member 202.

When the retention member 202 is placed in the secured position, the upper edges 235 of the sidewalls 231 forming the first vent portion 234a of the venting path 234 (FIG. 3) are made to contact the conical shaped portion 316 of the sleeve 304. In this position, the proximal face of the conical shaped portion 316 lays over the first vent portion 234a and the first vent cutout 236 of the venting path 234. The first vent portion 234a and the first vent cutout 236 may become substantially or partially covered by the contact. Similarly, in this embodiment, the second and third vent cutouts 238, 240 may become partially or substantially covered by the inner wall 309 of the catheter chamber 306. However, the integrity of the venting path 234 is maintained since the vent cutouts 238, 240 and the first portion 234a of the venting path on the distal facing surface of the retention member 202 are below the upper edges 235 of the body 204.

Similarly, when the cone shaped washer 320 is placed on the proximal facing surface 208 of the retention member 202, the upper edges 235 of the sidewalls 231 forming the second vent portion 234b of the venting path 234 are made to contact a distal facing surface of the conically shaped washer 320. In this embodiment, the first portion 234b of the venting path 234 and the fourth vent cutout 242 may become substantially or partially covered by the contact with the washer 320. However, the integrity of the venting path 234 is maintained since the fourth vent cutout and the second portion 234b on the proximal facing surface are below the upper edges 235 of the body 204.

In accordance with an operational embodiment, the needle 110 is introduced into a vein using the fully assembled catheter assembly 100 as shown in FIGS. 1A and 4. The assembled catheter assembly 100 includes the tubular catheter 104 positioned over the needle 110 and with the retention member 202 seated in the transition section 308 with the retention section 310 inside the catheter chamber 306. As the needle tip 116 moves to a location proximal of the distal end of the catheter tube, blood flows under pressure into the annular space between the outer wall of the needle 110 and the inner wall of the tubular catheter 104. Air contained within the tubular catheter 104 may be forced by the blood through the venting path 234 between the distal facing side and the proximal facing side of the retention member 202. Because of the relatively long venting path length, blood is kept within the venting path 234 of the retention member 202 for a period of time long enough to remove the needle 110 and needle guard 130, if used, from the catheter hub 106 to permit subsequent attachment of appropriate tubing set or the like to the catheter hub.

The above description presents the best mode contemplated for carrying out the present catheter assembly with the retention member in such full, clear, concise, and exact terms as to enable any person skilled in the art to which it pertains to make and use the retention member. This catheter assembly with the retention member is, however, susceptible to modifications and alternate constructions from that discussed above that are equivalent. For example, the retention member may be positioned in a separate hub that is then coupled to the catheter hub in a three-hub assembly, which includes the catheter hub, the needle hub, and the third retention housing. The needle assembly may also be modified by positioning the retention member in a catheter hub but placing a needle shield or tip protector in a separate hub located completely outside or partially outside of the catheter hub. In still yet other examples, the retention member may be made from multiple parts that are integrally assembled together. The tip protector may similarly be made from multiple parts that are integrally assembled together. Consequently, this catheter assembly is not limited to the particular embodiments disclosed. On the contrary, this catheter assembly covers all modifications and alternate constructions coming within the spirit and scope of the catheter assembly as generally expressed by the following claims, which particularly point out and distinctly claim the subject matter of the catheter assembly. Also, while certain features are expressly discussed for one another but not another, the discussed features may be used in other embodiments. i.e., interchangeable, provided the functions are compatible.

What is claimed is:

1. An intravenous (IV) catheter introducer assembly comprising a catheter hub having an interior surface defining an interior cavity and a retention member located inside the interior cavity and fixedly retained in an axial direction to the interior surface of the catheter hub; said retention member having an interior wall surface defining a bore having a needle located therein, said retention member having a longitudinal length of X and a venting path length comprising surface sections formed on an exterior of the retention member for venting gas of at least 2X, and wherein X is number representing a length, and wherein the needle contacts the interior wall surface defining the bore.

2. The intravenous catheter introducer assembly of claim 1, wherein the venting path length comprises a spiral path length and is enclosed in part by the interior surface of the catheter hub.

3. The intravenous catheter introducer assembly of claim 2, wherein the venting path length comprises a radial path length and an axial channel both formed on the exterior surface of the retention member.

4. The intravenous catheter introducer assembly of claim 1, wherein the venting path length comprises a spiral path length formed on an exterior surface and an interior surface of the retention member.

5. The intravenous catheter introducer assembly of claim 1, further comprising:
a tubular member extending distally from the catheter hub and defining a lumen, the lumen being in fluid communication with the interior cavity of the catheter hub and the tubular member extending along a lengthwise axis; and
a needle hub attached to a proximal end of the needle and the needle extending through the lumen of the tubular member.

6. The intravenous catheter introducer assembly of claim 5, wherein the retention member comprises a plurality of base walls of increasing diameters from a distal end towards a proximal direction.

7. The intravenous catheter introducer assembly of claim 5, wherein the retention member comprises a plurality of base walls of decreasing diameters from a proximal end towards a distal direction formed on an interior surface thereof.

8. The intravenous catheter introducer assembly of claim 5, further comprising a retention washer having a conical surface in contact with the retention member.

9. The intravenous catheter introducer assembly of claim 5, further comprising a needle guard disposed in the interior cavity of the catheter hub to cover a needle tip of the needle.

10. The intravenous catheter introducer assembly of claim 1, wherein the venting path length is at least 3X and comprises a non-linear vent path formed along an exterior surface of the retention member.

11. An intravenous (IV) catheter introducer assembly comprising:
a catheter hub having an exterior surface and an interior surface defining an interior cavity;
an introducer needle comprising a sharp distal tip, a shaft, and a proximal end attached to a needle hub;
a tubular member extending distally from the catheter hub having a length and a lumen having the introducer needle disposed therein; and
a retention member disposed within the interior cavity of the catheter hub, said retention member having a body having a central lumen sealed against the introducer needle, the retention member having a surface feature formed as a conic helix traversing on an exterior surface of the retention member defining a vent path.

12. The catheter introducer assembly of claim 11, wherein a proximal surface of the retention member comprises a plurality of base walls of decreasing diameters from a proximal end to a distal end of the retention member.

13. The catheter introducer assembly of claim 11, wherein the vent path comprises a venting channel length greater than a longitudinal length of the retention member.

14. The catheter introducer assembly of claim 13, wherein the venting channel length is greater than 120% of the longitudinal length of the retention member.

15. The catheter of device of claim 13, wherein the venting channel length is about 25 mm to about 45 mm in length.

16. The catheter introducer assembly of claim 11, wherein the central lumen comprises a distal surface diameter, an internal diameter and a proximal surface diameter.

17. A method for assembly a catheter assembly comprising:
mounting a needle comprising a needle tip, a shaft, and a proximal end to a needle hub;
mounting a catheter tube with a lumen to a catheter hub, the catheter hub comprising an interior surface defining an interior cavity;
fixing a retention member in the interior cavity of the catheter hub so that the retention member is fixed from moving along an axial direction, the retention member comprising a bore, a distally facing surface, and a proximally facing surface;
placing the needle through the bore of the retention member and through the lumen of the catheter tube; and
wherein the retention member comprises a longitudinal length of X and a venting path length formed on an exterior surface thereof of at least 2X, and wherein X is number representing a length.

18. The method of claim 17, further comprising mounting a retention washer inside the interior cavity of the catheter hub adjacent the retention member.

19. The method of claim 18, further comprising engaging the retention washer to a bump formed on the interior surface of the catheter hub.

20. The method of claim 17, further comprising placing a tip protector on the needle to cover the needle tip when removing the needle in a proximal direction.

21. The method of claim 17, wherein the venting path length is at least 3X and comprises a non-linear vent path formed along the exterior surface of the retention member.

* * * * *